United States Patent [19]

Farooq

[11] Patent Number: 5,403,955

[45] Date of Patent: Apr. 4, 1995

[54] MORDANTS FOR INK-JET RECEPTORS AND THE LIKE

[75] Inventor: Omar Farooq, Woodbury, Minn.

[73] Assignee: Minnesota Mining and Manufacturing Company, Saint Paul, Minn.

[21] Appl. No.: 234,247

[22] Filed: Apr. 28, 1994

[51] Int. Cl.$^6$ .................. C07F 9/54; C07C 281/18; C09B 67/00; G03C 8/00

[52] U.S. Cl. .............................. 564/15; 8/551; 8/554; 430/213; 430/941; 564/227; 564/228

[58] Field of Search ............ 8/551, 554; 430/213, 430/941; 564/15, 227, 228

[56] References Cited

U.S. PATENT DOCUMENTS

| | | | |
|---|---|---|---|
| 2,945,006 | 7/1960 | Minsk | 260/65 |
| 3,075,841 | 1/1963 | Lehman et al. | 96/77 |
| 3,271,148 | 9/1966 | Whitmore | 96/29 |
| 3,429,839 | 2/1969 | Franco | 260/8 |
| 3,547,649 | 12/1970 | Franco | 96/114 |
| 4,379,838 | 4/1983 | Helling et al. | 430/518 |
| 4,450,224 | 5/1984 | Klein et al. | 430/213 |
| 4,500,631 | 2/1985 | Sakamoto et al. | 430/413 |
| 4,695,531 | 9/1987 | Delfino et al. | 430/513 |
| 4,814,255 | 3/1989 | Vanmaele et al. | 430/213 |
| 4,820,608 | 4/1989 | Claeys et al. | 430/213 |
| 4,855,211 | 8/1989 | Janssens et al. | 430/213 |

FOREIGN PATENT DOCUMENTS

| | | |
|---|---|---|
| 931270 | 10/1972 | Italy . |
| 63-307979 | 12/1988 | Japan ............... B41M 5/00 |
| 850281 | 10/1960 | United Kingdom . |

Primary Examiner—Peter O'Sullivan
Attorney, Agent, or Firm—Gary L. Griswold; Walter N. Kirn; Thomas C. Lagaly

[57] ABSTRACT

Novel mordants based upon a polyethyleneimine backbone and either pendant phosphonium or quaternized-nitrogen compounds are disclosed. The mordants find use in stopping or controlling ink-bleeding into ink-jet receptors and photographic films.

12 Claims, No Drawings

MORDANTS FOR INK-JET RECEPTORS AND THE LIKE

FIELD OF THE INVENTION

This invention relates to mordants for ink-jet receptors and the like and more particularly, it relates to various types of novel mordants based upon a polyethyleneimine backbone.

BACKGROUND OF THE ART

The basic polymeric mordants useful to mordant a dye in a hydrophilic colloidal layer between a base and a photographic emulsion layer disclosed in U.S. Pat. No. 4,695,531 comprise repeating units of formula:

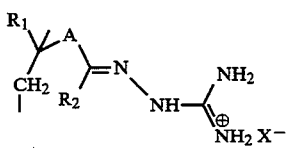
I wherein: $R_1$ is hydrogen or a methyl group; A is a —COO— or a —COO-alkylene group, e.g., —COOCH$_2$—, —COOCH$_2$CH$_2$—; $R_2$ is a hydrogen or a lower alkyl group having from 1–4 carbon atoms; and X is an anion, e.g., acetate, oxalate, sulfate, chloride, or bromide. Mordant I can comprise units derived from vinylic monomers, for example, acrylates, acrylamides, vinylacetates, styreries, vinyl ethers, vinyl ketones, vinyl alcohols, unsaturated chlorides, and nitriles with the proviso that such copolymerizable units be in a quantity of up to 10–20% by weight. Similar mordants with the exclusion of A in I are also disclosed in GB Patent No. 850,281.

Polymeric mordants prepared by polymerizing or copolymerizing vinyl pyridine or alkyl vinyl pyridine are also known in the art (see, for example, Italian Patent No. 931,270).

Polyvinylpyridine-based mordants, e.g., II

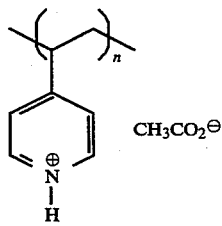
II are also known in the art (see U.S. Patent No. 4,695,531).

Non-diffusive mordants based on poly(N-vinylimidazole) of the type III are known in the art (see U.S. Pat. No. 4,500,631) and have been used in certain radiographic image-forming processes wherein the mordants were coupled with water-soluble dyes. Polymeric mordants of the type III as well as IV are also disclosed in Japanese Publn. No. 63-307979.

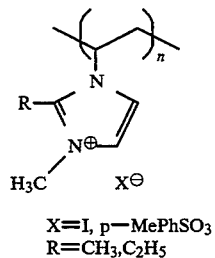
III

X=I, p—MePhSO$_3$
R=CH$_3$, C$_2$H$_5$

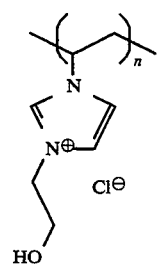
IV

Examples of other polymeric mordants useful in the photographic arts which incorporate ammonium or guanidinium groups are disclosed in U.S. Pat. Nos. 2,945,006; 3,075,841; 3,271,148; 4,379,838; and 4,814,255.

Other types of polymeric mordants for dyes are also known in the imaging arts. For example, U.S. Pat. No. 3,429,839 discloses polymeric mordants having pendant groups V, such as the mordant of formula VI:

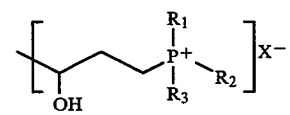
V

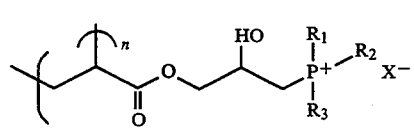
VI wherein: $R_1$, $R_2$, and $R_3$ are alkyl, aryl, aralkyl groups, or any two of the R substituents are part of a 5- or 6-membered heterocyclic ring and X is an anion, usually an anion of a mineral acid or a carboxylic acid having from 2 to 20 carbon atoms.

U.S. Pat. No. 3,547,649 discloses polymeric mordants of the following formulae:

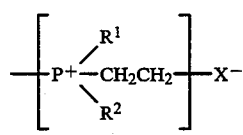
VII

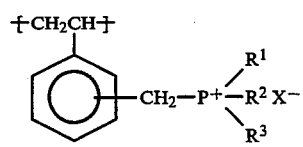
VIII wherein: $R^1$, $R^2$, and $R^3$ are alkyl, aryl, aralkyl or any two of the R substituents are part of a 5- or 6-membered heterocyclic ring and X is an anion.

Other patents which disclose quaternary phosphonium groups which have been incorporated into various polymeric systems and used as mordants for dyes include U.S. Pat. Nos. 4,379,838; 4,855,211; and 4,820,608.

Because of the advent of ink-jet printers, there is a continued demand in the industry for mordants which will control or stop ink-bleeding into ink-jet receptors and the like. It was against this background that research for such novel mordants was conducted.

SUMMARY OF THE INVENTION

The present invention provides novel mordants for dyes and the like. In one embodiment, the inventive mordants are based upon a polyethyleneimine backbone, with either quaternary phosphonium or guanidinium pendant groups, as represented by the following formula:

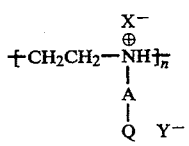

wherein: A is an alkylene radical; Q is $P^{\oplus}R_3$ or

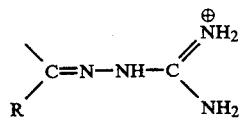

wherein R is an alkyl, aryl, aralkyl, or alkaryl group; n is an integer of 2 or greater, and X and Y are independently anions. Preferably, A is a $C_1$ to $C_{10}$ alkylene group. More preferably, A is an alkylene radical of the formula $+C-H_2+_m$ wherein m is an integer of from 1 to 10.

More preferably, m is an integer of from 1 to 4.

In accordance with another embodiment of the present invention, there is provided a class of inventive mordants of the formula:

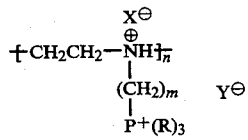

IX wherein: R is an alkyl, aryl, aralkyl, or alkaryl group; m is an integer of from 1 to 10; n is an integer of 2 or greater; and X and Y are independently anions, preferably $CH_3SO_3$, Br, $NO_3$, Cl, $CF_3COO$,

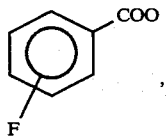

p-MePhSO$_3$, ClO$_4$, F, CF$_3$SO$_3$, BF$_4$, C$_4$F$_9$SO$_3$, FSO$_3$, PF$_6$, ClSO$_3$, or SbF$_6$. Preferably, R is aryl. More preferably, R is phenyl.

In accordance with still another embodiment of the present invention, there is provided a class of inventive mordants of the formula:

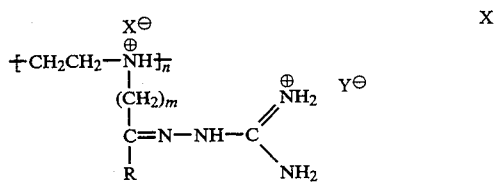

wherein: R, m, n, X, and Y are as defined earlier herein broadly with respect to formula IX. Preferably, R is a $C_1$-$C_4$ alkyl group. More preferably, R is methyl.

The inventive mordants described above are believed to be novel and not to have been previously disclosed in the literature. The inventive mordants are useful in a variety of applications such as in ink-jet formulations to control or stop ink-bleeding into ink-jet and photographic films.

As is well understood in this area, substitution is not only tolerated, but is often advisable. As a means of simplifying the discussion and recitation of certain terminology used throughout this application, the terms "group" and "moiety" are used to differentiate between chemical species that allow for substitution or which may be substituted and those which do not so allow or may not be so substituted. Thus, when the term "group" is used to describe a chemical substituent, the described chemical material includes the basic group and that group with conventional substitution. Where the term "moiety" is used to describe a chemical compound or substituent, only an unsubstituted chemical material is intended to be included. For example, the phrase "alkyl group" is intended to include not only pure open-chain and cyclic saturated hydrocarbon alkyl substituents, such as methyl, ethyl, propyl, t-butyl, cyclohexyl, adamantyl, octadecyl, and the like, but also alkyl substituents bearing further substituents known in the art, such as hydroxyl, alkoxy, vinyl, phenyl, halogen atoms (F, Cl, Br, and I), cyano, nitro, amino, carboxyl, etc. On the other hand, the phrase "alkyl moiety" is limited to the inclusion of only pure open-chain and cyclic saturated hydrocarbon alkyl substituents, such as methyl, ethyl, propyl, t-butyl, cyclohexyl, adamantyl, octadecyl, and the like.

Other aspects of the present invention are apparent from the detailed description, the examples, and the claims.

DETAILED DESCRIPTION OF THE INVENTION AND EXAMPLES

EXAMPLE 1

This example describes the synthesis of mordant IX(a) shown below:

(a) To a solution of 4g 4-bromobutyltriphenylphosphonium bromide (available from Aldrich Chemical Co.) in 40 ml methylene chloride under reflux was added a solution of 0.70 g polyethyleneimine (PEI) (50%) (available from BASF Corp.) in 4 ml methylene chloride. The reaction mixture was refluxed for 14 hrs., cooled, and the mordant was precipitated from acetone to obtain a dry material in 50% yield.

(b) The procedure in (a) was repeated for 6 hrs. and the material was precipitated from ether to obtain the mordant in 77 % yield.

(c) The reaction described in procedure (a) was repeated for 4 hrs. in methanol by reverse addition (the system is exothermic) and the material was precipitated from ether to obtain the mordant in 95 % yield.

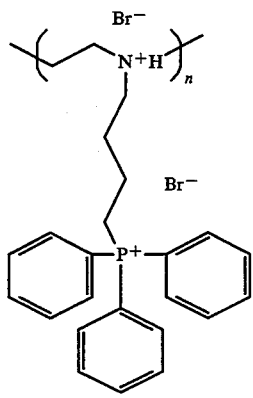

IX(a)

EXAMPLE 2

This example describes the synthesis of mordant IX(o) shown below:

To a solution of 1.04g PEI (BASF) in 30 ml methanol was added 5.7 g of 3-bromopropyltriphenylphosphonium bromide (Aldrich). The reaction mixture was refluxed for 4 hrs., cooled, and the reaction product was precipitated from ether to obtain mordant IX(b) in 93 % yield. $^1$H NMR spectra confirmed the following structure:

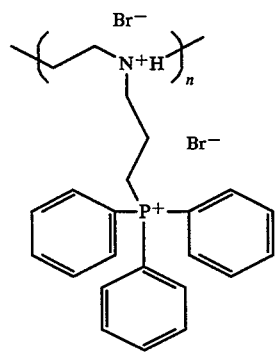

IX(b)

EXAMPLE 3

The procedure in Example 2 was repeated using chloromethyltriphenylphosphonium chloride (Aldrich) instead of the 3-bromopropyltriphenylphosphonium bromide salt and the material was precipitated from ether to obtain the mordant IX(c) in 90% yield.

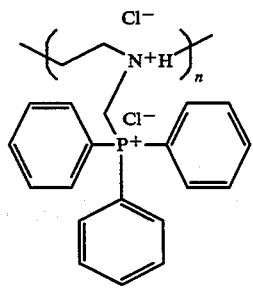

IX(c)

EXAMPLE 4

This example describes the synthesis of mordant X having a variety of different anions as shown below.

To a solution of 4 g PEI in 30 g methanol was added a solution of chloroacetone hydrazone of aminoguanidinium hydrochloride in 15 ml methanol. The chloroacetoneohydrazone of aminoguanidinium hydrochloride solution was prepared by adding 7 g chloroacetone under stirring to an aqueous solution of 8 g aminoguanidinium hydrochloride (available from Wilshire Chemical) in 20 g water. The solution was heated to 40° C. for 10 mins. and then cooled to 5° C. for 4-6 hours. The chloroacetone-hydrazone of aminoguanidinium hydrochloride was precipitated out as a crystalline material which was filtered and dried to a yield of 96%. The solution was briefly heated to about 45° C. Mordant X(a) was precipitated from ether and dried in vacuo. Other mordants X(b)–(i) were similarly prepared by using chloroacetone hydrazone of aminoguandinium salt with an appropriate counterion as shown below.

| Mordant | | |
|---|---|---|
| X | (a) | Y = Cl |
| X | (b) | Y = CF$_3$CO$_2$ |
| X | (c) | Y = CF$_3$SO$_3$ |
| X | (d) | Y = CH$_3$—⌬—SO$_3$ |
| X | (e) | Y = BF$_4$ |
| X | (f) | Y = PF$_6$ |
| X | (g) | Y = C$_2$F$_5$CO$_2$ |
| X | (h) | Y = C$_3$F$_7$CO$_2$ |
| X | (i) | Y = F—⌬—CO$_2$ |

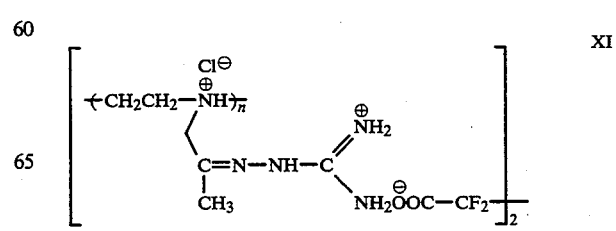

X

EXAMPLES 5

Mordants XI and XII shown below were prepared in accordance with the procedure described in Example 4 except that PEI and the hydrazone of the appropriate dianion were used at a 2:1 molar ratio.

XI

-continued

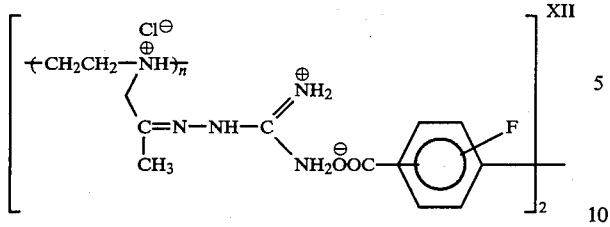

Reasonable modifications and variations are possible from the foregoing disclosure without departing from either the spirit or scope of the present invention as defined in the claims.

What is claimed is:

1. A mordant, comprising a polyethyleneimine backbone with two or more pendant groups, of the formula:

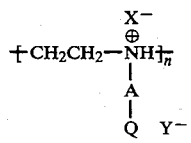

wherein: A is an alkylene radical; Q is $P^{\oplus}R_3$ or

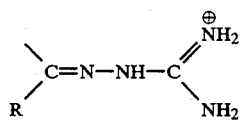

wherein R is an alkyl, aryl, aralkyl, or alkaryl group; n is an integer of 2 or greater; and X and Y are independently anions.

2. The mordant of claim 1 wherein A is $-(CH_2)_m-$ and m is an integer of from 1-10.

3. The mordant according to claim 2 wherein m is an integer of from 1-4.

4. The mordant according to claim 1 wherein X and Y are independently $CH_3SO_3$; Br; $NO_3$; Cl; $CF_3COO$;

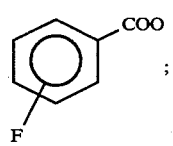

p-MePhSO$_3$; ClO$_4$; F; CF$_3$SO$_3$; BF$_4$; C$_4$F$_9$SO$_3$; FSO$_3$; PF$_6$; ClSO$_3$; or SbF$_6$.

5. A mordant of the formula:

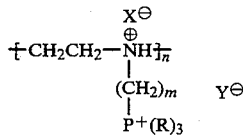

wherein: R is an alkoil, aryl, aralkyl, or alkaryl group; m is an integer of from 1 to 10; n is an integer of 2 or greater; and X and Y are independently anions.

6. The mordant of claim 5 wherein R is aryl.

7. The mordant of claim 6 wherein R is phenyl.

8. The mordant of claim 5 wherein X and Y are independently $CH_3SO_3$; Br; $NO_3$; Cl; $CF_3COO$;

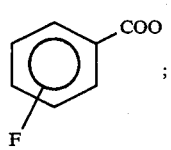

p-MePhSO$_3$; ClO$_4$; F; CF$_3$SO$_3$; BF$_4$; C$_4$F$_9$SO$_3$; FSO$_3$; PF$_6$; ClSO$_3$; or SbF$_6$.

9. A mordant of the formula:

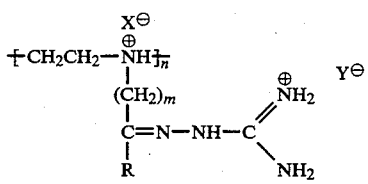

wherein: R is an alkyl, aryl, aralkyl, or alkaryl group; m is an integer of from 1 to 10; n is an integer of 2 or greater; and X and Y are independently anions.

10. A mordant according to claim 9 wherein R is an alkyl group of 1–4 carbon atoms.

11. The mordant according to claim 10 wherein R is methyl.

12. The mordant according to claim 9 wherein X and Y are independently $CH_3SO_3$; Br; $NO_3$; Cl; $CF_3COO$;

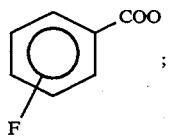

p-MePhSO$_3$; ClO$_4$; F; CF$_3$SO$_3$; BF$_4$; C$_4$F$_9$SO$_3$; FSO$_3$; PF$_6$; ClSO$_3$; or SbF$_6$.

* * * * *

UNITED STATES PATENT AND TRADEMARK OFFICE
CERTIFICATE OF CORRECTION

PATENT NO.   : 5,403,955
DATED        : April 4, 1995
INVENTOR(S)  : Omar Farooq It is certified that error appears in the above-indentified patent and that said Letters Patent is hereby corrected as shown below:

In the claims, at column 8, line 9, delete the word "alloil" and insert therefor --alkyl--.

Signed and Sealed this

Twenty-ninth Day of August, 1995

Attest:

BRUCE LEHMAN

Attesting Officer     Commissioner of Patents and Trademarks